(12) United States Patent  (10) Patent No.: US 7,008,055 B2
McLear et al.  (45) Date of Patent: Mar. 7, 2006

(54) EYE PROTECTION METHODS AND APPARATUS

(75) Inventors: Mark McLear, Attleboro Falls, MA (US); Tobias Gerfin, Wattwil (CH)

(73) Assignee: GPT Glendale, Inc., Smithfield, RI (US)

( * ) Notice: Subject to any disclaimer, the term of this patent is extended or adjusted under 35 U.S.C. 154(b) by 0 days.

(21) Appl. No.: 10/745,580

(22) Filed: Dec. 29, 2003

(65) Prior Publication Data

US 2004/0190106 A1  Sep. 30, 2004

Related U.S. Application Data

(60) Provisional application No. 60/455,583, filed on Mar. 19, 2003.

(51) Int. Cl.
 *G02C 7/10* (2006.01)
 *G02F 1/1335* (2006.01)

(52) U.S. Cl. .......................... 351/44; 349/14
(58) Field of Classification Search ............. 351/44, 351/41, 45; 349/13, 14
 See application file for complete search history.

(56) References Cited

U.S. PATENT DOCUMENTS

| | | | |
|---|---|---|---|
| 3,137,784 A | 6/1964 | Käsemann | 351/44 |
| 3,245,315 A | 4/1966 | Marks et al. | 351/44 |
| 4,240,709 A | 12/1980 | Hornell | 359/352 |
| 4,241,286 A | 12/1980 | Gordon | 219/147 |
| 4,462,661 A | 7/1984 | Witt | 349/14 |
| 4,491,390 A | 1/1985 | Tong-Shen | 349/116 |
| 4,560,239 A | 12/1985 | Katz | 349/14 |
| 4,758,079 A | 7/1988 | Bledsoe | 351/44 |
| 4,759,608 A | 7/1988 | Yang | 349/14 |
| 5,067,795 A | 11/1991 | Senatore | 349/14 |
| 5,074,647 A | 12/1991 | Fergason et al. | 349/14 |
| 5,172,256 A | 12/1992 | Sethofer et al. | 349/14 |
| 5,184,156 A | 2/1993 | Black et al. | 351/158 |
| 5,208,688 A | 5/1993 | Fergason et al. | 349/14 |
| 5,252,817 A | 10/1993 | Fergason et al. | 250/205 |
| 5,276,539 A | 1/1994 | Humphrey | 349/14 |
| 5,315,099 A | 5/1994 | Gunz et al. | 250/201.1 |
| 5,412,439 A | 5/1995 | Horn | 351/45 |
| 5,463,428 A | 10/1995 | Lipton et al. | 351/158 |
| 5,519,522 A | 5/1996 | Fergason | 349/14 |
| 5,552,841 A | 9/1996 | Gallorini et al. | 351/49 |
| 5,589,101 A | 12/1996 | Khoo | 252/299.01 |
| 5,760,852 A | 6/1998 | Wu et al. | 349/14 |
| 5,793,449 A | 8/1998 | Lagerwall | 349/14 |
| 5,841,507 A | 11/1998 | Barnes | 359/49 |
| 5,877,825 A | 3/1999 | Kotler | 349/14 |
| 5,880,793 A | 3/1999 | Gunz et al. | 349/14 |
| 6,008,466 A | 12/1999 | Hosoda | 349/14 |
| 6,021,520 A | 2/2000 | Wang-Lee | 2/8 |
| 6,067,129 A | 5/2000 | Fergason | 351/14 |

(Continued)

*Primary Examiner*—Huy Mai
(74) *Attorney, Agent, or Firm*—Oliff & Berridge, PLC (57) ABSTRACT

An eye protection apparatus includes a selectively darkenable element, such as a liquid crystal panel, and a controller that causes transmission of a darken signal that causes the selectively darkenable element to darken in conjunction with an emission of light, such as intense diffuse light that is used in some medical procedures. Protection against both laser light and diffuse light may be provided in the same eye protection apparatus. The darken signal may be transmitted prior to the emission of the diffuse light, and cause the selectively darkenable element to achieve a darkened state prior to emission of the diffuse light.

60 Claims, 8 Drawing Sheets

U.S. PATENT DOCUMENTS

| | | | |
|---|---|---|---|
| 6,097,451 A | 8/2000 | Palmer et al. | 349/14 |
| 6,128,123 A | 10/2000 | Wagner | 359/260 |
| 6,168,278 B1 | 1/2001 | Mukai | 359/612 |
| 6,170,947 B1 | 1/2001 | Colles et al. | 351/44 |
| 6,378,133 B1 | 4/2002 | Daikuzono | 2/9 |
| 6,483,090 B1 | 11/2002 | Bae | 250/201.1 |
| 6,501,443 B1 | 12/2002 | McMahon | 345/52 |
| 2001/0038491 A1 | 11/2001 | Fergason | 359/466 |

EYE PROTECTION METHODS AND APPARATUS

This nonprovisional application claims the benefit of U.S. Provisional Application No. 60/455,583, filed Mar. 19, 2003.

BACKGROUND OF THE INVENTION

1. Field of Invention

This invention relates to methods and apparatus for protecting eyes from light radiation, particularly in connection with, but not limited to, medical procedures.

2. Description of Related Art

Various medical procedures involve the generation of bright and/or intense light from which human eyes must be shielded in order to avoid retinal damage, temporary vision loss from visual overload, and/or headaches or nausea that can result from prolonged exposure to such light. Various procedures are now being performed, are under development, or will be developed that use laser light or high intensity pulses of diffuse light. Examples of such medical procedures include hair removal procedures, tattoo removal procedures, skin regeneration procedures and dental procedures.

In recent years, auto-darkening technology has been used in the welding industry. Such auto-darkening technology may include an optical sensor and a liquid crystal panel that is switchable between a "see-through" or "light" state, in which a wearer can see clearly through the panel in normal ambient light conditions, and a "darkened" state, in which only a small amount of light passes through to allow the wearer safely to view a source of very bright and/or intense light such as the light emitted during an arc welding process. The liquid crystal panel enters the "darkened" state when the optical sensor detects a flash of intense light.

In medical procedures, the doctor or technician performing the procedure typically uses passive dark eyewear to protect his or her eyes from a laser light source or high intensity diffuse light source. Thus, the doctor or technician typically views the target, puts on the passive dark eyewear, irradiates the target with the light source, takes off the eyewear, and then views the effect of the irradiation.

U.S. Pat. No. 5,877,825 to Kotler discusses certain disadvantages of safety glasses that block only a specific wavelength of pulsed laser radiation used in industrial, medical and scientific applications, and discloses safety glasses in which an electro-optic shutter is provided which, when applied with a voltage signal, switches from a transparent state to an opaque state within a response time. A voltage signal is applied at an operational time interval that is slightly longer than the response time so that, by the time of emission of each radiation pulse, the electro-optic shutter is in the opaque state. Kotler discloses that an IR transmitter and detector may be used for a wireless connection between the safety glasses and a laser.

U.S. Pat. No. 6,170,947 to Colles et al. discloses a system for protection from light generated by interaction of laser energy with matter, for use in medical applications and particularly in dental applications. The light protection system includes one or more optical elements that are placed in an active, i.e., light blocking, state in response to an electrical signal. This signal initiates optical element activation approximately one millisecond before firing of a lasing apparatus, which is the approximate time for the one or more optical elements to transform from an inactive state to the active state.

Neither the Kotler patent nor the Colles patent discloses a system for protecting against intense diffuse light in a medical procedure.

SUMMARY OF THE INVENTION

In the case of permanently dark eyewear, the person performing the procedure is not able to view the target immediately after the light flash ceases, which is particularly disadvantageous in medical procedures, and causes delay because the person performing the procedure must put on the eyewear, perform the procedure, take off the eyewear, view the work area, put the eyewear back on if further performance of the procedure is necessary, and so on. Although selectively darkenable eyewear has been provided for some applications, e.g., welding and laser operations, the prior art has not provided a selectively darkenable apparatus that, in a darkened state, protects a wearer's eyes from intense diffuse light used in a medical procedure.

Additionally, a doctor or technician who uses both diffuse light and laser light must, according to the prior art, have separate eyewear (e.g., goggles or glasses) for each procedure. This adds expense, and has the additional drawback that the doctor or technician must become accustomed to the feel of two different goggles or glasses, rather than just one.

Additionally, while the prior art discloses an infrared (IR) wireless connection between a laser and safety glasses, IR may have a disadvantage particularly in the medical field because IR signals can interfere with the operation of other machines such as monitors or the like.

In embodiments, this invention provides eye protection methods and apparatus in which a trigger signal that triggers an emission of light is detected, and a darken signal is transmitted that causes a selectively darkenable element to darken in conjunction with the emission of the light. Preferably, the selectively darkenable element is pre-triggered so as to achieve a darkened state at the same time as, or just prior to, emission of the light. Software and/or hardware may be used to implement the pre-trigger.

The light may be diffuse light, and may be in the form of light pulses, such as Intense Pulse Light (IPL). In embodiments, a combination eye protection apparatus is provided that protects against both diffuse light and laser light.

In embodiments, the darken signal is sent via a transmission path that is, at least in part, a wireless transmission path. Thus, the darken signal may be a wireless signal such as an optical, acoustic, or electromagnetic signal. In other embodiments, the darken signal is sent via a wired (including electrical or optical cable) transmission path.

Some medical treatments or procedures involving the use of diffuse light involve only a brief, intense flash of the diffuse light. The physician or technician positions a light emitting tool at the desired position and causes the light to flash, but does not move the light emitting tool during the emission of the light. Thus, the physician or technician may not need to be able to see the light emitting device or the work area during the light emission. Other medical treatments or procedures may involve a more steady stream of diffuse light, typically in the form of a series of pulses, that lasts for a second, several seconds, or more and the physician or technician may need to be able to see the light emitting device or the work area during or immediately after the light emission.

Most medical treatments or procedures involving the use of laser light involve a steady state or pulsed laser beam over a somewhat extended period of time, such as several seconds or more, and it would be advantageous if the physician or technician were able to see the work area at least intermittently during the entire process.

This invention also provides eye protection methods and apparatus that protect against both diffuse light and laser light. The diffuse light protection is preferably "active" protection provided by a selectively darkenable element, such as an auto-darkening device that darkens in association with emission of light. The laser light protection is preferably "passive" protection that is constantly in effect, and may be provided by, for example, a dye material incorporated in a lens or lenses of an eye protection device or a coating applied to one or more surfaces of the lens system.

This invention also provides eye protection methods and apparatus that, in a medical treatment or procedure involving intense diffuse light, protect the eyes of a physician or technician from the intense diffuse light by optically detecting the diffuse light and causing a selectively darkenable element to darken in response to the detection of light.

This invention also provides eye protection methods and apparatus that use acoustic transmission of a darken signal to cause a selectively darkenable element to darken in conjunction with the emission of light. The acoustic signal does not interfere with the operation of other machines such as monitors or the like that may be used in the same environment as the selectively darkenable element.

These and other objects, advantages and salient features of the invention are described in or apparent from the following detailed description of exemplary embodiments.

BRIEF DESCRIPTION OF THE DRAWINGS

Exemplary embodiments of the invention will be described with reference to the drawings, wherein like numerals represent like parts and wherein.

DETAILED DESCRIPTION OF PREFERRED EMBODIMENTS

This invention protects eyes from intense diffuse light, particularly intense diffuse light used in a medical procedure, by causing one or more selectively darkenable elements to be placed in a darkened state in conjunction with emission of the intense diffuse light. The darkened state may be achieved just before, at the same time as, or just after emission of the light. The invention may also protect eyes from one or more specific wavelengths of laser light.

Figure 1:
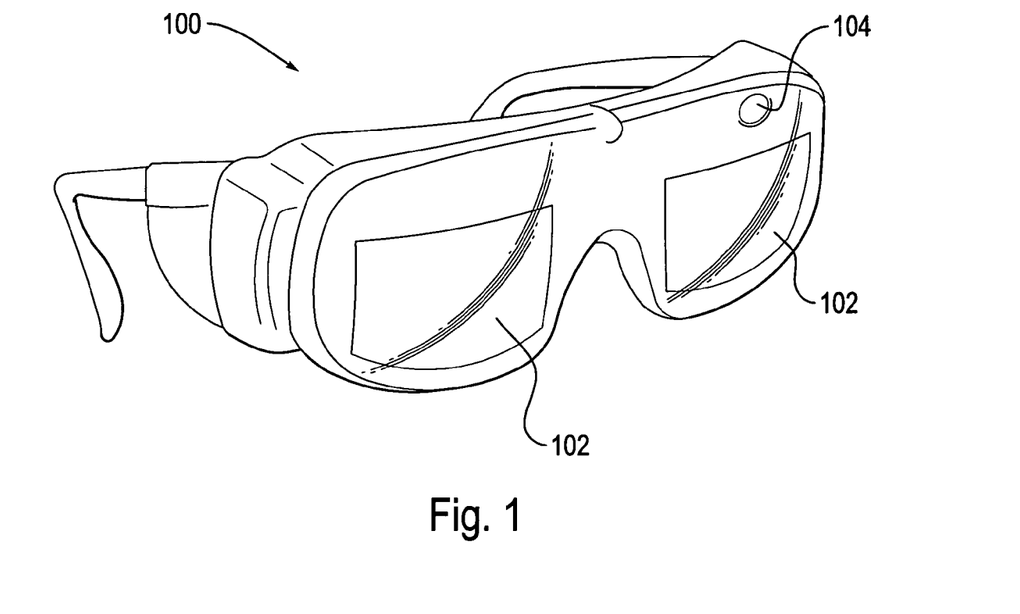
FIG. 1 is a front perspective view of an eye protection device according to the invention.

FIG. 1 is a front perspective view of an embodiment of an eye protection device 100 according to the invention. The eye protection device 100 is constituted by goggles or glasses that include selectively darkenable elements 102, such as liquid crystal panels, at positions corresponding to the positions of a wearer's eyes. A darken signal receiver 104 is provided on the eye protection device 100, through which a darken signal is received as described in more detail hereafter. The selectively darkenable elements 102 are normally in a see-through state, in which the wearer can see clearly through the selectively darkenable elements 102 in normal ambient light conditions. When power is applied to the selectively darkenable elements 102, they are placed in a darkened state. A "darkened" state, as used herein, refers either to a completely opaque state or a substantially opaque state, in which no light or substantially no light passes through, or to a state in which a small amount of light may pass through but the wearer's eyes are protected, i.e., the wearer can safely view the light without sustaining damage or discomfort, or to a state in which selected wavelengths or ranges of wavelengths of light are blocked, but other wavelengths are allowed to pass.

Known or later developed liquid crystal panels or the like, or other known or later developed darkenable elements, may be used as the selectively darkenable elements 102. It will be appreciated that, rather than providing two separate selectively darkenable elements 102 as shown, a single selectively darkenable element may be provided and configured to protect both eyes of the wearer.

When the selectively darkenable elements 102 are in the see-through state, the eye protection device 100 preferably has a visible light transmission (VLT) of about 10% or greater, such as at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, with 100% being the theoretical ideal. As one example, selectively darkenable elements designed for use only with intense diffuse light may have a VLT of from about 15% to about 20% in the see-through state, and selectively darkenable elements designed for use with both intense diffuse light and laser light may have a VLT of from about 50% to about 65% in the see-through state. When the selectively darkenable elements 102 are in the darkened state, the eye protection device 100 preferably has a visible light transmission VLT of no more than 5%, preferably about 1% or less and more preferably about 0.1% or less, such as from about 0.01% to about 0.05%. Preferably, in the darkened state, the eye protection device 100 meets American National Standards Institute (ANSI) standard ANSI Z87.1, 1989, R98 for minimum "welding shade 8.5 or 9." Additionally or alternatively, the selectively darkenable elements 102 may be set, in the darkened state, only to be "darkened" with respect to particular wavelengths or ranges of wavelengths of light.

Additionally, the eye protection device 100 may be specifically structured to protect against one or more specified wavelengths, or a range of wavelengths, of light.

The eye protection device 100 preferably protects against both diffuse light, such as Intense Pulse Light (IPL), and laser light, such as Yttrium Aluminum Garnet (YAG) laser light ($\lambda=1{,}064$ nm), diode laser light (($\lambda=600$–$700$ nm or $750$–$1{,}000$ nm) and/or gallium arsenide laser light ($\lambda=800$–$860$ nm).

In providing both diffuse light and laser light protection, there exists the following difficulty. A selectively darkenable element that, in the darkened state, provides sufficient protection against diffuse light may, in the undarkened state, be too dark to allow visibility of laser light and/or a work area.

One solution to this problem is to provide a selectively darkenable element with at least three states, e.g., a see-through state, a semi-darkened state that protects against laser light and a darkened state that protects against diffuse light. In this solution, the type of light can be automatically distinguished so that the appropriate one of the semi-darkened state and the darkened state can be activated, or the user may, through a switch, manually set the type of light to be used. It may be difficult to use optical detection to trigger the laser-protective state, i.e., the semi-darkened state, because laser light is typically in a narrow beam and may not reflect onto an optical detector. However, by detecting the generation of the laser light based on an activation signal, e.g., a trigger signal, the laser light may be indirectly detected and an appropriate signal may be sent to the eye protection device to place the darkenable element in the semi-darkened state. Detection of diffuse light, either directly (e.g., by an optical detector) or indirectly (e.g., by detection of an activation signal) can be used to cause a different signal to be sent to the eye protection device to place the darkenable element in the semi-darkened state.

Another solution is to provide an eye protection device with "active" diffuse light protection and "passive" laser light protection. "Active" protection generally refers to protection that is selectively in effect, e.g., only in effect when intense light is being generated or is about to be generated. A darkenable eye protection device, such as an auto-darkening device that darkens in association with the light, is an example of active protection. In contrast, "passive" protection is constantly in effect, and may be provided by, for example, a dye material incorporated in a lens of an eye protection device, as may be done using methods and materials known to those skilled in the art, or a coating applied to a surface of the lens, as may also be done by methods and materials known to those skilled in the art. Such a dye or coating is typically effective at screening a particular wavelength or range of wavelengths of light, and is very useful for protecting against laser light because laser light typically has a particular wavelength depending on the type of laser.

The latter solution is preferable in terms of having a less complicated and, typically, a less expensive, structure. However, in embodiments, if a dye or coating is applied to the lens, some degree of visibility may be sacrificed, particularly at certain wavelengths or ranges of wavelength, and thus it becomes more difficult to see through the lens in the see-through state.

Therefore, according to the invention, a laser protective dye or coating may be applied to the lens of the eye protection device 100, but the dye or coating, or the density or concentration thereof, is selected to be such that, in the see-through state, the eye protection device has a visible light transmission (VLT) of at least 10%, such as at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, with 100% being the theoretical ideal. As one example, the VLT is from about 50% to about 65% in the see-through state. Provided that the dye or coating remains effective at screening the particular wavelength or wavelengths of the laser or lasers to be used, coating thickness, concentration or other parameters of the dye or coating may be varied as needed to obtain sufficient or optimal VLT.

Some selectively darkenable elements are provided with one or more infrared (IR) filter coatings. When a laser protective dye or coating is applied, these one or more IR filter coatings are preferably omitted or removed, or else the eye protection device 100 may be too dark, even in the see-through state, to allow good visibility of the work area and/or the light device 300. Therefore, in embodiments, the eye protection device 100 is free of IR filter coatings. Furthermore, when a laser protective dye or coating is applied, a dye or coating is preferably selected such that only a single wavelength, e.g., 1,064 nm in the case of a YAG laser, or a narrow range of wavelengths, are screened. This avoids unnecessary reduction of visibility.

Figure 2:
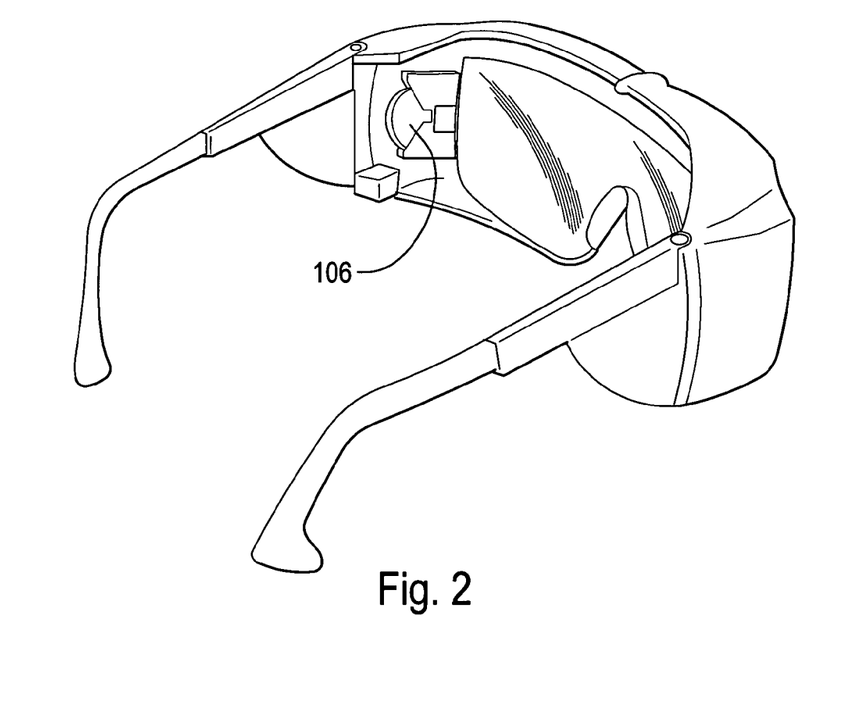
FIG. 2 is a rear perspective view of the eye protection device of Fig.

FIG. 2 is a rear perspective view of the eye protection device 100 of FIG. 1. A battery 106 may be held in the frame of the eye protection device 100, and provide power to drive the selectively darkenable elements 102 into a darkened state. If the eye protection device 100 is hard-wired to a controller or power source, as in the embodiment shown in FIG. 7, discussed below, electricity may be supplied through the wire.

As shown in FIGS. 1 and 2, the eye protection device 100 is preferably contoured to generally match the contour of a wearer's face. When a bright flash of diffuse light is generated in front of the wearer's eyes, the light will reflect off surrounding walls, equipment and the like. The contoured shape of the eye protection device 100 helps restrict such reflected light from entering the wearer's eyes. To further restrict such reflected light, the side portions, e.g., the temples, of the eye protection device 100 are preferably darkened or opaque.

Figure 3:
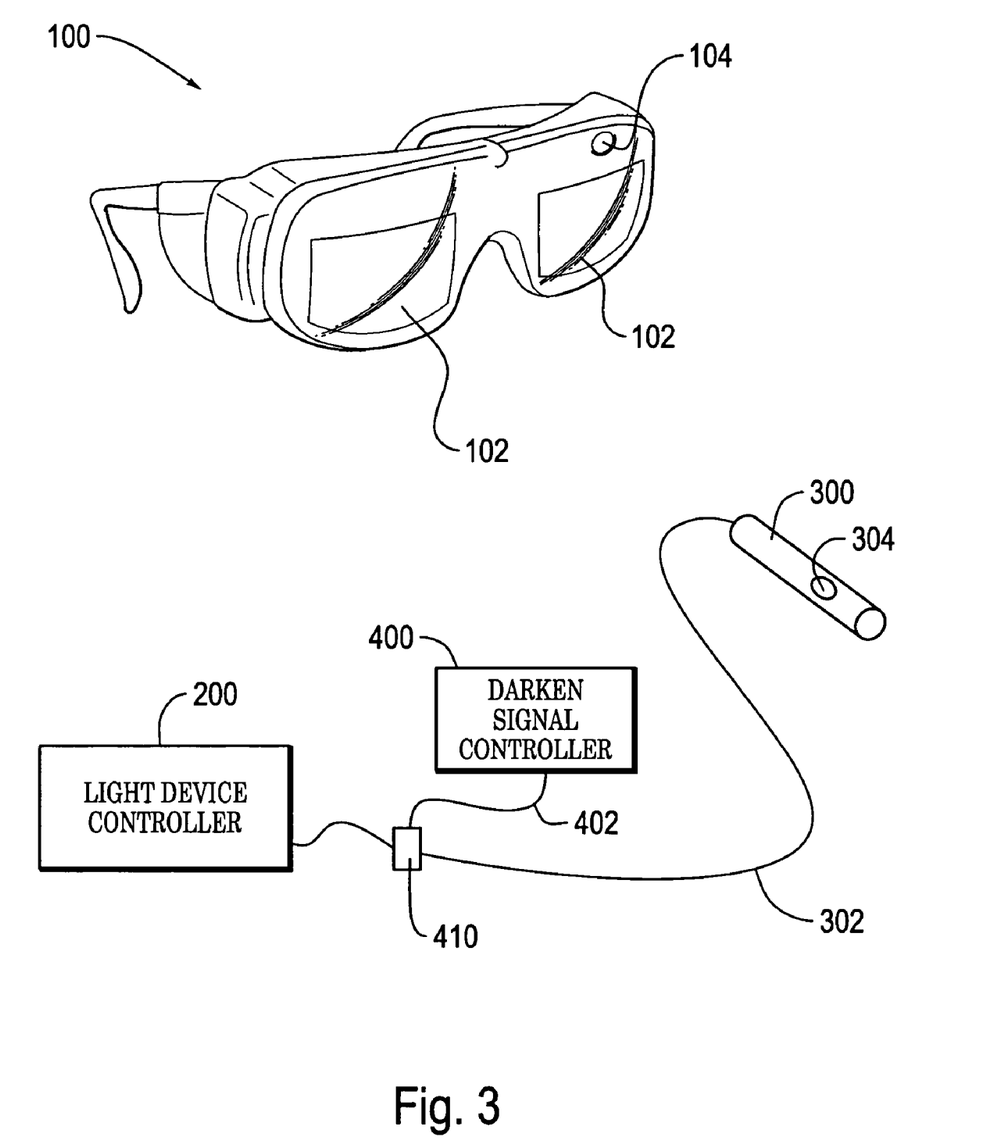
FIG. 3 illustrates a first exemplary system according to the invention.

FIG. 3 illustrates a first exemplary system according to the invention. This system includes the eye protection device 100 shown in FIGS. 1 and 2, a light device controller 200, a light emission device 300 (referred to hereafter as "light device 300"), and a darken signal transmitter 400. In accordance with the foregoing discussion, the eye protection 100 has selectively darkenable elements 102 for protecting against intense diffuse light. Optionally, active protection against laser light is provided by the selectively darkenable elements 102 and/or passive protection against laser light is provided by a dye or coating. In the following discussion, it is assumed that if laser light protection is provided, it is provided passively. Therefore, the selectively darkenable elements 102 only darken in response to intense diffuse light. However, this does not limit the invention, and those skilled in the art will understand how to make any modifications necessary for adaptation to active laser protection, e.g., by selection of darkenable materials specific to the wavelength of a selected laser.

The light device 300 is connected to the light device controller 200 via a link 302, which typically includes an electrical conductor capable of transmitting electrical signals and/or electrical power to the light device 300, but which may alternatively be a wireless link, also referred to below as a "wireless path," over which control signals and/or power from a power source (not shown) is transmitted to the light device 300, e.g., by a wireless signal such as an optical, acoustic or electromagnetic signal. If the light device 300 is battery powered or otherwise separately connected to a power source, the light device controller 200 may only transmit control signals. The link 302 could also be or include an optical waveguide. Hereafter, for convenience, the terms "wired link" and "wired path" shall encompass electrical conductors, such as electrical cables, optical waveguides, such as fiber optic cables, pneumatic, hydraulic, mechanical, or any other suitable type of connection. In short, the link 302 may be any path by which the light device 300 communicates with the light device controller 200.

The light device 300 may emit laser light or diffuse light in response to operation of a switch 304. In FIG. 3, the switch 304 is provided on the light device 300 itself, but the switch alternatively may be, for example, a foot-operated switch or the like that is separate from the light device 300, or may be on or associated with, e.g., separately connected to, the light device controller 200.

The darken signal transmitter 400 is capable of detecting transmission of a signal and/or power over the link 302. For example, when the link 302 is an electrically conductive cable, a device 410 may detect current passing through the link 302, and transmit current to the darken signal transmitter 400 in response thereto via a link 402, which typically also includes an electrically conductive cable, but which may also be or include an optical waveguide or a wireless transmission path, a pneumatic, hydraulic or mechanical connection, or any other path over which communication is possible. The device 410 may, for example, be an inductive coil-type pick-up device or a simple signal splitter. It should be appreciated that the darken signal transmitter 400 may also have a separate link to a power source.

The darken signal transmitter 400 transmits a signal to the darken signal receiver 104 of the eye protection device 100 when a signal or current is detected passing through the link 302, thereby causing the selectively darkenable elements 102 to change to a darkened state.

Those skilled in the art will understand how to arrange the particular structure such that the darkenable elements 102 remain in the darkened state while light is being emitted from the light device 300, and are placed in the see-through state when light is not being emitted from the light device 300. For example, if current continues to flow through the link 302 during light emission, then the darken signal transmitter 400 may keep detecting this current and keeping transmitting a darken signal, or a continuous series of darken signals, to the eye protection device 100 for as long as the light emission lasts.

As another example, the darken signal transmitter 400 may detect a first control signal that activates the light device 300 (e.g., when the light device switch 304 is placed in the "ON" state), and detect a second control signal when the light device stops emitting light (e.g., when the light device switch 304 is placed in the "OFF" state), but not detect any current between the first and second control signals (e.g., while the light device 300 is actually emitting light). In this case, the darken signal transmitter 400 may send a first darken signal to the eye protection device 100 when the first control signal is detected, to change the selectively darkenable elements 102 to the darkened state, and send a second signal to the eye protection device 100 when the second control signal is detected, to change the selectively darkenable elements 102 back to the see-through state. The first darken signal and the second signal may be identical signals, and the eye protection device 100 may simply toggle between the darkened state and the see-through state each time a signal is received. Alternatively, the first darken signal and the second signal may be different signals, e.g., the first darken signal may be a one-pulse signal and the second signal may be a two-pulse signal, and the eye protection device 100 may distinguish the signals and change the selectively darkenable elements 102 to the appropriate state based on the type of signal that is received.

As another example, the eye protection device 100 may, in addition to the darken signal receiver 104, have a photodetector (not shown) that detects light emitted by the light device 300. In this case, the darken signal transmitter 400 may detect a control signal that activates the light device 300, but not detect any current while the light device 300 is actually emitting light or when the light device switch 304 is placed in the "OFF" state. The selectively darkenable elements 102 are changed to the darkened state when the darken signal receiver 104 receives a darken signal from the darken signal transmitter 400, and are kept in the darkened state for as long as the photodetector (not shown) continues to detect light emitted by the light device 300.

Figure 7:
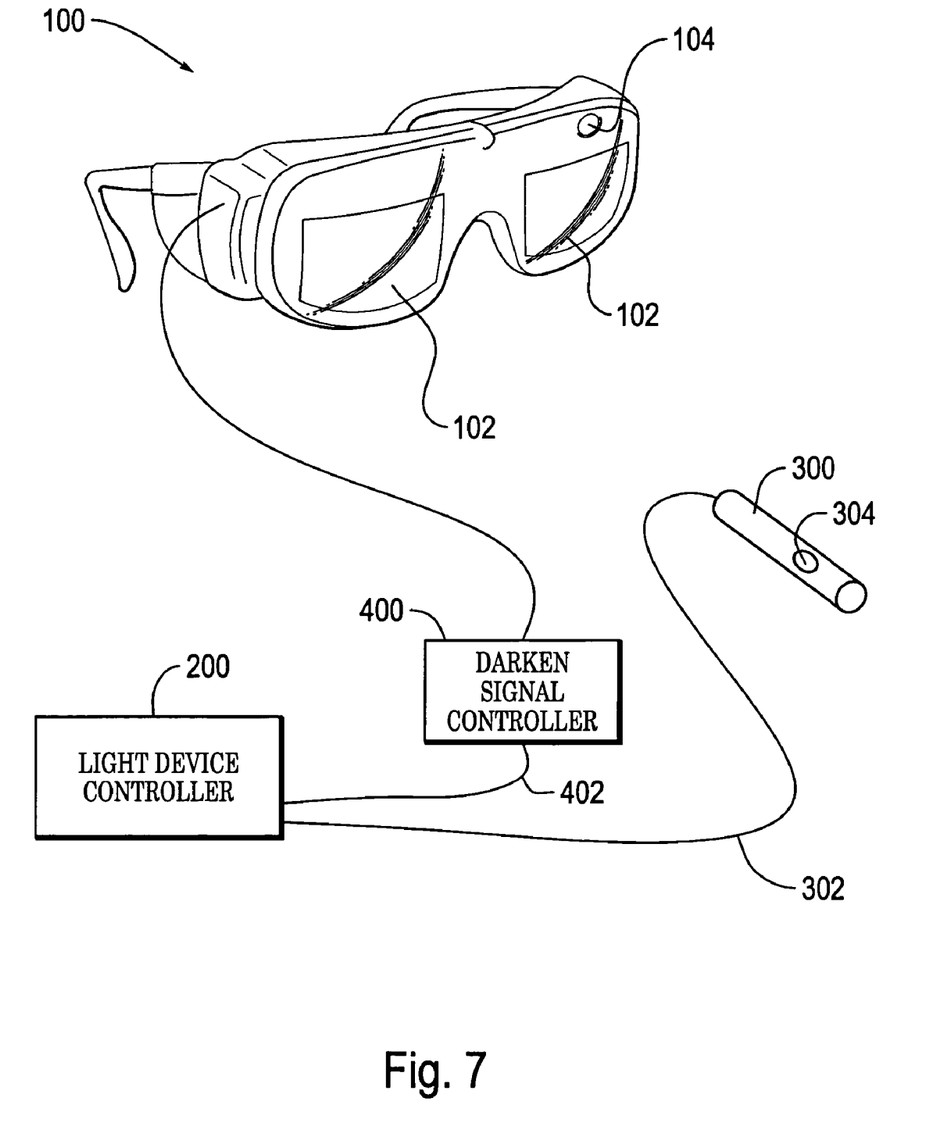
FIG. 7 illustrates a third exemplary system according to the invention.

The transmission path by which darken signals are transmitted from the darken signal transmitter 400 to the eye protection device 100 may be a wireless link. Types of wireless transmission include acoustic signals, optical signals such as infrared (IR) signals, and electromagnetic signals such as radio frequency (RF) signals. Thus, for example, the darken signal transmitter 400 may be an acoustic signal transmitter, an optical signal transmitter or an electromagnetic signal transmitter, and the darken signal receiver 104 of the eye protection device 100 may be a corresponding acoustic signal receiver, optical signal receiver or electromagnetic signal receiver. The transmission path alternatively may be a wired link, for example as shown in FIG. 7 and discussed in more detail below. As with the link 302 discussed above, the terms "wired link" and "wired path" shall encompass both electrical conductors, such as electrical cables, and optical waveguides, such as fiber optic cables. The "wired link" alternatively may be or include a pneumatic, hydraulic, mechanical, or any other suitable type of connection, and, in short, may be any path by which a signal may be communicated.

An advantage of an acoustic transmitter as the darken signal transmitter 400 is that acoustic waves have less tendency to interfere with the operation of other equipment, e.g., medical equipment or the like, than optical waves or electromagnetic waves. The acoustic wave may have a frequency of, for example, 20 kHz, or any other appropriate frequency Preferably, a frequency is selected that is substantially different from other frequencies that may be generated by equipment or the like in the intended environment of use, so as to avoid accidental or unintentional darkening of the selectively darkenable elements 102 via "stray" or "incidental" signals from such equipment.

It may be desirable to shorten the response time of the selectively darkenable elements 102, e.g., shorten the time required from the time a change-causing voltage is applied to the selectively darkenable elements 102 to the time the selectively darkenable elements 102 actually achieve the darkened state. For example, one way to shorten the response time is to initially drive the selectively darkenable elements 102 with a relatively high voltage, and then drop back to a lower voltage. In one example, the selectively darkenable elements 102 are initially driven at about 18 V for about 1 ms, and then the driving voltage drops to about 6–7 V. Another way is to pre-heat the selectively darkenable elements 102 with a built-in heating element or the like (not shown), particularly when the selectively darkenable elements 102 include liquid crystal, because liquid crystal is more responsive at higher temperatures.

Shortening the response time can be particularly beneficial in systems in which the darkening of the selectively darkenable elements 102 occurs in response to optical detection of light emitted by the light device 300, for the following reason. In such a system, the darkening necessarily begins to occur just after the flash of intense light begins. Thus, although typically not discernable by the brain, a brief, intense flash of light may enter the eyes before the darkened state has been achieved. Therefore, any reduction of the response time correspondingly reduces the amount of intense, potentially harmful light that enters the eyes.

More preferable, in terms of reducing or preventing entry of intense, potentially harmful light into the eyes, are "pre-triggered" systems in which, when light is emitted by the light device 300, the selectively darkenable elements 102 of the eye protection device 100 are caused to achieve the darkened state at the same time as, or slightly before, the emission of the light. In "pre-triggered" systems, the selectively darkenable lens elements 102 are "pre-triggered," i.e., caused to start to darken before the flash of light begins, so that the darkened state is achieved at the same time, or slightly before, the flash of light appears. Pre-triggering will be described in more detail with reference to FIG. 4.

Figure 4:
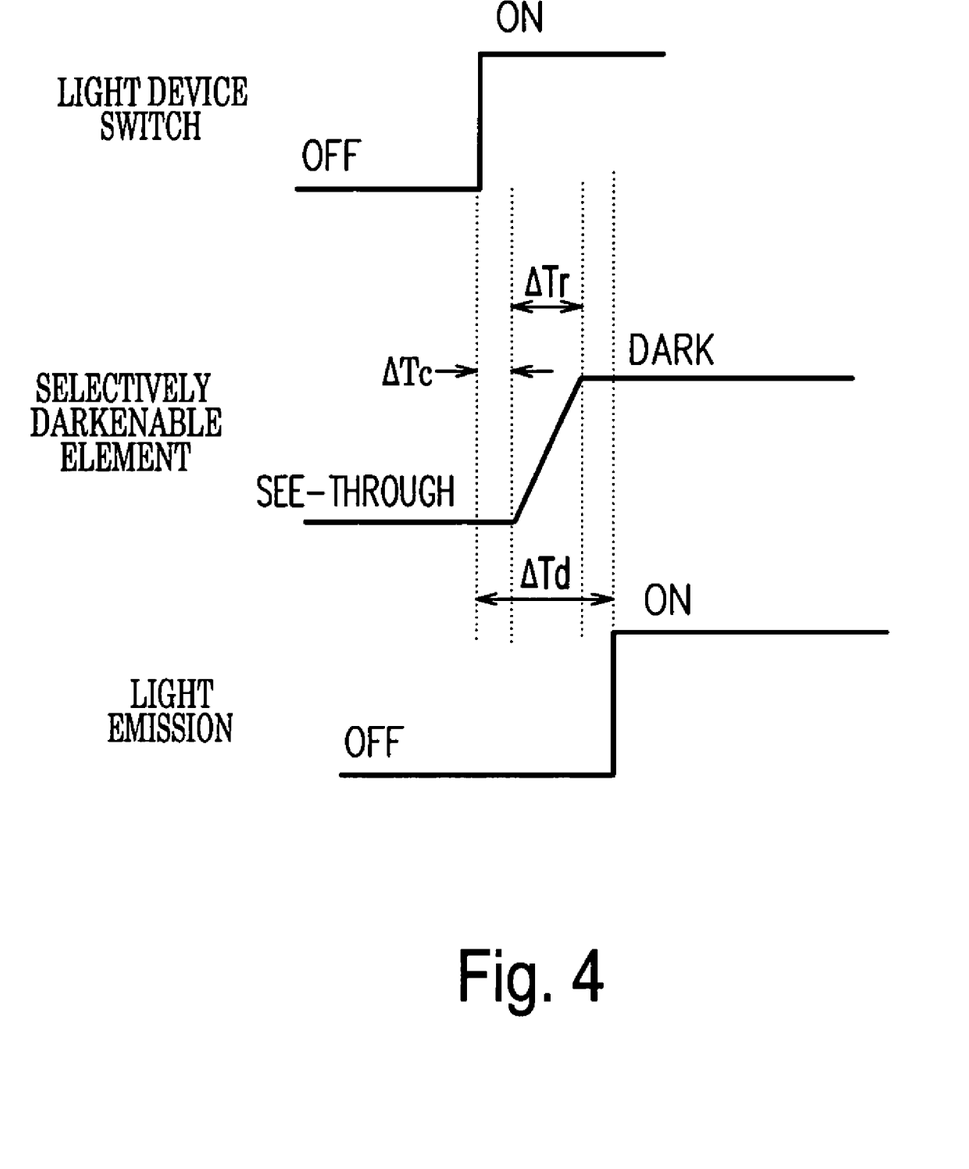
FIG. 4 is a timing chart illustrating pre-triggering of a darkenable element.

FIG. 4 is a timing chart illustrating certain forms of pre-triggering of the selectively darkenable elements 102. As shown, the selectively darkenable elements are activated at time $\Delta Tc$ after the light device switch is placed in the "ON" state. $\Delta Tc$ represents the time required for detection of the light device switch "ON" state and for an activation signal to be sent to the selectively darkenable elements. It should be appreciated that the "light device switch," as used herein, is what the operator uses to manifest to the system a desire for light to be emitted. The switch that directly causes light to be emitted may be this switch, or another switch. If another switch is what directly causes light to be emitted, then the light device switch actuated by the operator basically acts as a relay, and it should also be appreciated that any number of other relays may be positioned between the light device switch and the switch that directly causes light emission. $\Delta Tr$ represents time required for the selectively darkenable elements to achieve the darkened state, once activated. $\Delta Td$ represents the total delay time from the point at which the light device switch is placed in the "ON" state to the point at which light emission commences. Preferably, $\Delta Td \geq \Delta Tc + \Delta Tr$.

An advantage of the system shown in FIG. 3 is that a darken signal transmitter 400 and an eye protector 100 may easily be retrofitted to an existing light device controller 200 and light device 300. For example, if the link 302 of the light device 300 connects to the light device controller 200 by a pin-type connector or the like, then, to install the darken signal transmitter 400, one may simply unplug the pin-type connector from the light device controller 400, plug in the device 410 (e.g., inductive coil-type pick-up device or signal splitter) to the light device controller 400, and plug the link 302 into the device 410.

Figure 5:
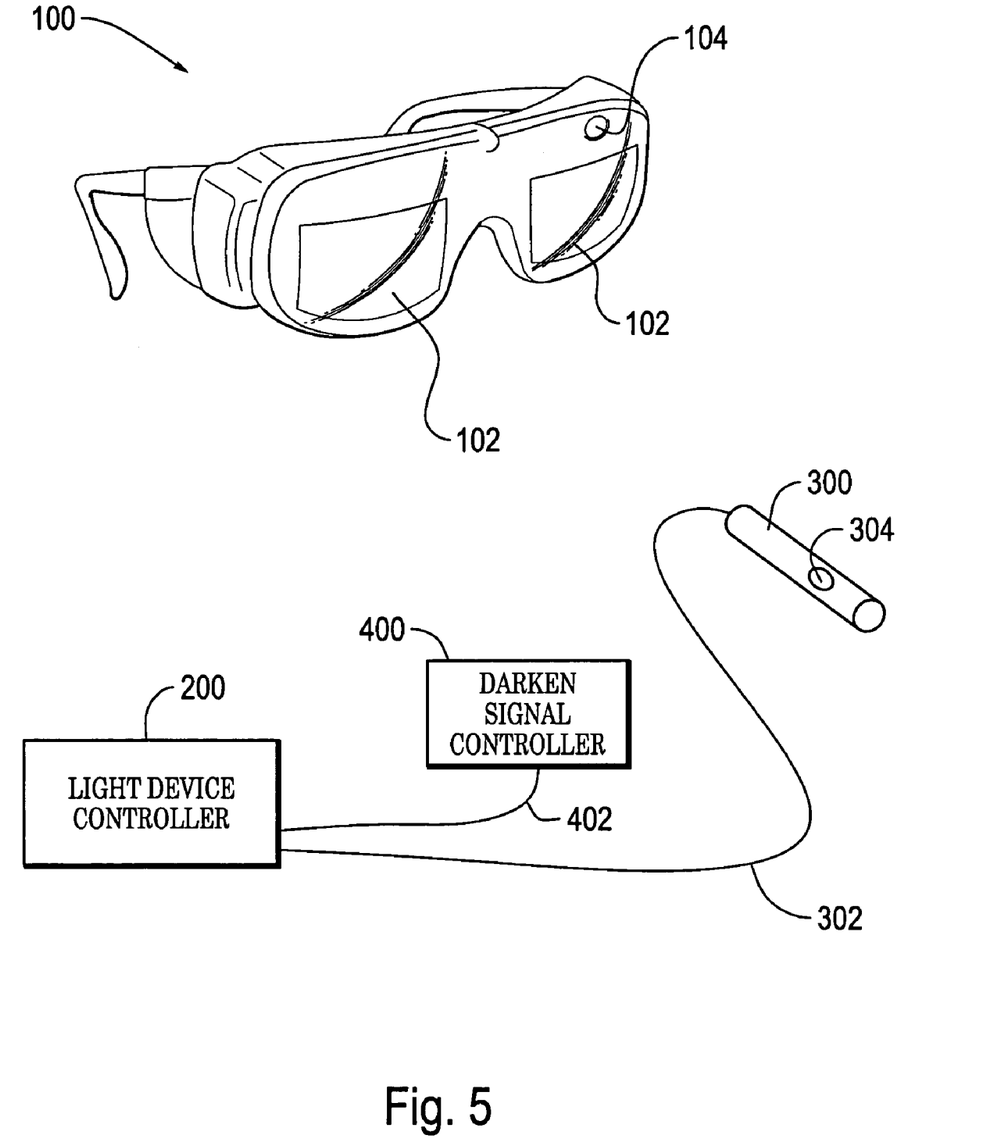
FIG. 5 illustrates a second exemplary system according to the invention.

FIG. 5 illustrates a second exemplary system according to the invention. The system shown in FIG. 5 is substantially the same as that shown in FIG. 3, except that the link 402 of the darken signal transmitter 400 is connected to internal circuitry of the light device controller 200, rather than being connected to the link 302 of the light device 300.

An advantage of the system shown in FIG. 5 is that, rather than being dependent on a signal or current flowing through the link 302, the same or different signals may be independently transmitted to the darken signal transmitter 400. Therefore, it is easy and highly reliable to achieve pre-triggering such as the pre-triggering depicted in FIG. 4.

For example, when the switch 304 of the light device 300 is placed in the "ON" state, the light device 300 may "request authorization" to emit light, e.g., by sending a signal to the light device controller 200, and the light device controller 200 may send a signal to the darken signal transmitter 400 to cause pre-triggering of the selectively darkenable elements 102 before "authorizing" the emission of light by the light device 300. Thus, a delay is effected and/or prolonged between the time that the switch 304 is placed in the "ON" state and the time that light begins to be emitted. If necessary or desired, this delay may be effected or prolonged using hardware, such as a delay circuit or a timer circuit, and/or software. An exemplary program for implementing the delay through software, and thereby implementing pre-triggering, is shown in FIG. 6.

Figure 6:
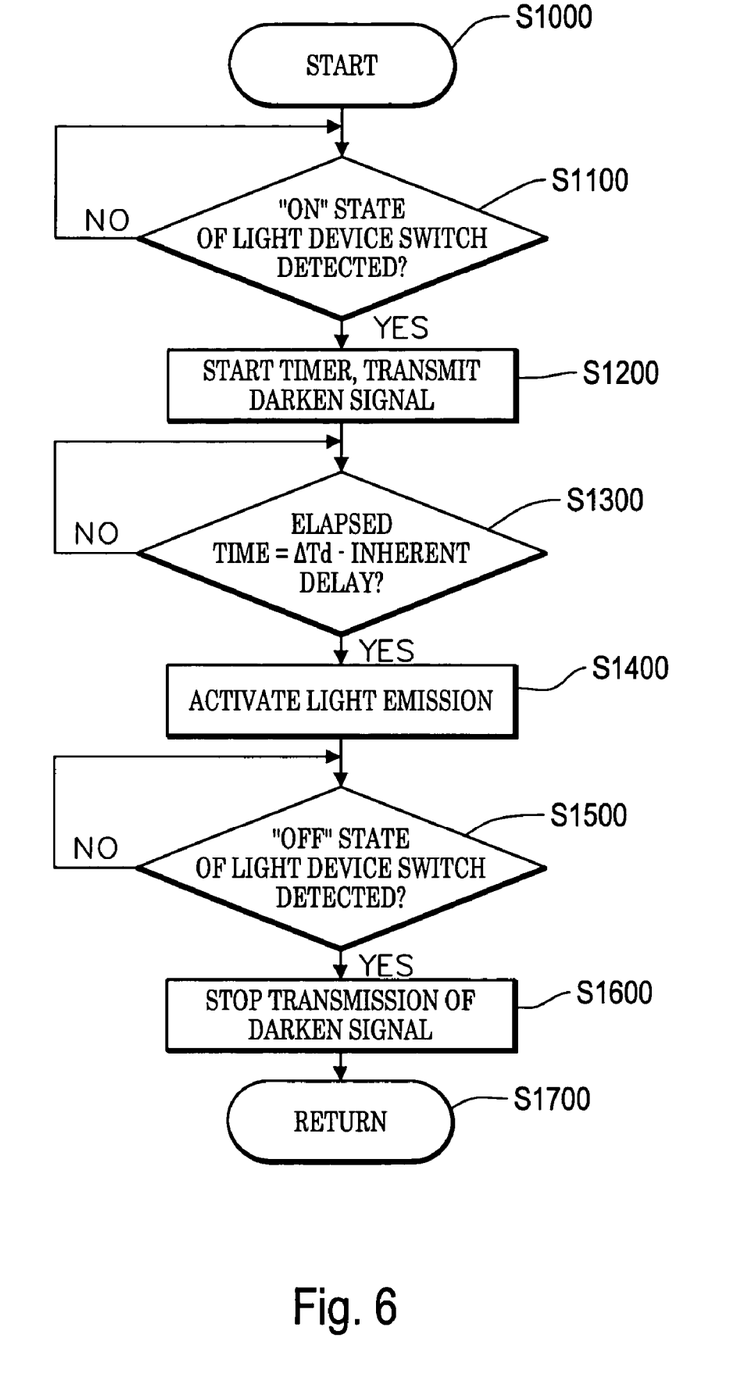
FIG. 6 is a flowchart illustrating an exemplary method according to the invention.

FIG. 6 is a flowchart illustrating an exemplary method of pre-triggering according to the invention. Beginning in step S1000, the process continues to step S1100, and determines whether an "ON" state of a light device switch is detected. Step S1100 is repeated until the "ON" state is detected, and then the process continues to step S1200.

In step S1200, a timer is started to measure elapsed time from the detection of the "ON" state of the light switch, and a darken signal is transmitted to selectively darkenable elements to cause the selectively darkenable elements to be placed in a darkened state.

Each system will have an inherent delay between the time light emission is activated, e.g., the time that an activation signal is generated by the light device controller, and the time that light emission actually begins. For example, referring to FIG. 5, this inherent delay may depend on the length and type of the link 302 between the light device controller 200 and the light device 300, and on the particular circuitry of the light device controller 200. This inherent delay may be calculated or determined empirically for each system, and a value representing the inherent delay may be stored. A typical inherent delay may, for example, be on the order of from about 1 $\mu s$ or less to about 100 $\mu s$ or more. If sufficiently small as to be deemed negligible by those skilled in the art, the inherent delay may be ignored.

In step S1300, it is determined whether the elapsed time is equal to the desired total delay time $\Delta Td$, from the point at which the light device switch is placed in the "ON" state to the point at which light emission commences, minus any inherent delay for that system. The process then continues to step 1400, and activates light emission, e.g., by sending a signal and/or electrical power to the light device 300. The light emission will actually begin after time $\Delta Td$ has elapsed. The process then continues to step S1500.

In step S1500, it is determined whether an "OFF" state of the light device switch is detected. Step S1500 is repeated until the "OFF" state is detected, and then the process continues to step 1600 and stops transmission of the darken signal, thereby allowing the selectively darkenable elements to return to a see-through state. The process then continues to step S1700 and returns to step S1000.

If the duration of light emission is predetermined, then the appropriate length of the darkened state may also be predetermined, and thus steps S1500 and S1600 may be omitted. For example, if each pressing of the light device switch 304 in FIG. 5 results in a single pulse of light, or a single series of pulses of light, lasting, e.g., from about 100 $\mu s$ or less to about two seconds or more, then the darkened state may be pre-set to last an appropriate length of time, e.g., at least as long as the single pulse of light, or the single series of pulses of light.

In some applications, it may be necessary or desirable for the darkened state to last longer than the pulse of light or series of pulses of light. For example, in industrial welding, there is often a very bright "afterglow" of molten metal for a brief time after the cessation of the welding operation, e.g., after the emission of light to electrical arcing has stopped, and it may be desirable for the darkened state to last, e.g., about one second longer than the emission of light in order to protect the wearer's eyes against this afterglow. Some known or later developed medical applications may produce a similar "afterglow." In a pulsed-light system in which the selectively darkenable elements 102 must be "re-triggered" after every pulse, or in a system in which the operator may separately activate several emissions of light in rapid succession, it is beneficial to have a darkened state longer, by a delay time, than a single pulse of pulsed light or a single emission of non-pulsed light because this allows time for a subsequent pulse to be triggered, or a subsequent emission to be triggered, before the selectively darkenable elements 102 return to the see-through state. For example, the delay time may be set at from about 0.1 second or less to about one second or more, such as at about 0.5 second. Furthermore, the delay time may be fixed, or may be adjustable, either step-wise or continuously, by the operator depending on the system to be used and/or on the operator's preference.

FIG. 7 illustrates a third exemplary system according to the invention. The system shown in FIG. 7 is substantially the same as that shown in FIG. 5, except that signals are transmitted from the darken signal transmitter 400 to the eye protection device 100 via a wired path, rather than a wireless path. It will be appreciated that the darken signal transmitter 400 in this embodiment need not be a separate entity from the light device controller 200, and may, for example, be implemented using software, as in the example shown in FIG. 6.

Figure 8:
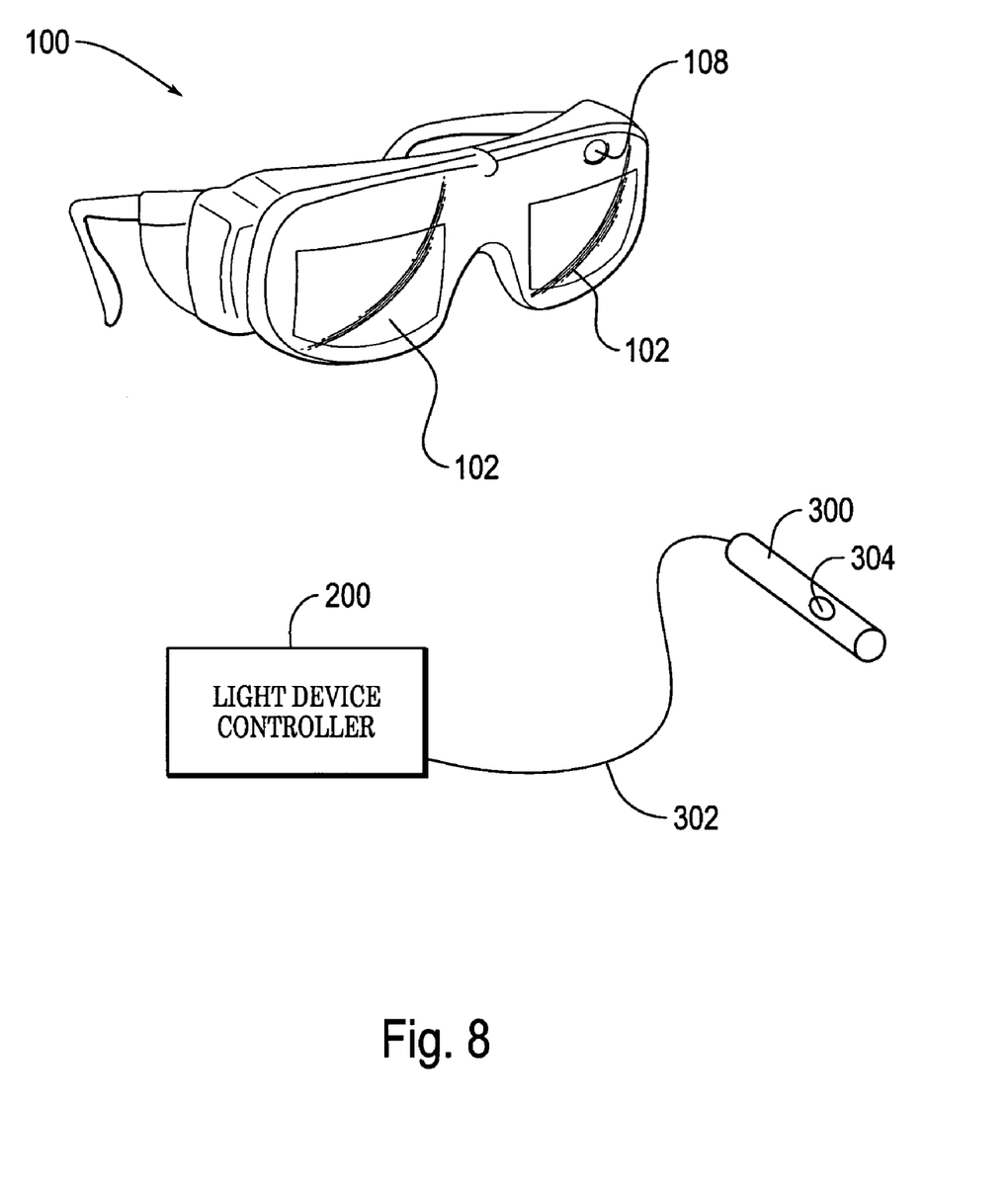
FIG. 8 illustrates a fourth exemplary system according to the invention.

FIG. 8 illustrates a fourth exemplary system according to the invention. Unlike the systems shown in FIGS. 3, 5 and 7, the system shown in FIG. 8 does not include a separate darken signal transmitter 400. Additionally, as the darken signal receiver, the eye protection device 100 has a photodetector 108 that detects light emitted by the light device 300.

Preferably, when the light device switch 304 is placed in the "ON" state, the light device initially emits a very brief pulse of light, preferably of relatively low intensity, to cause the selectively darkenable elements 102 to be placed in the darkened state. Immediately thereafter, a longer, more intense emission of light, that is, the "operating" light from the light device 300, occurs. Thus, even though some light will enter the wearer's eyes before the selectively darkenable elements 102 reach the darkened state, it will be less intense light than the operating light. However, in other embodiments, only the actual "operating" light may be emitted and the photodetector 108 may simply detect the "operating" light.

Figure 9:
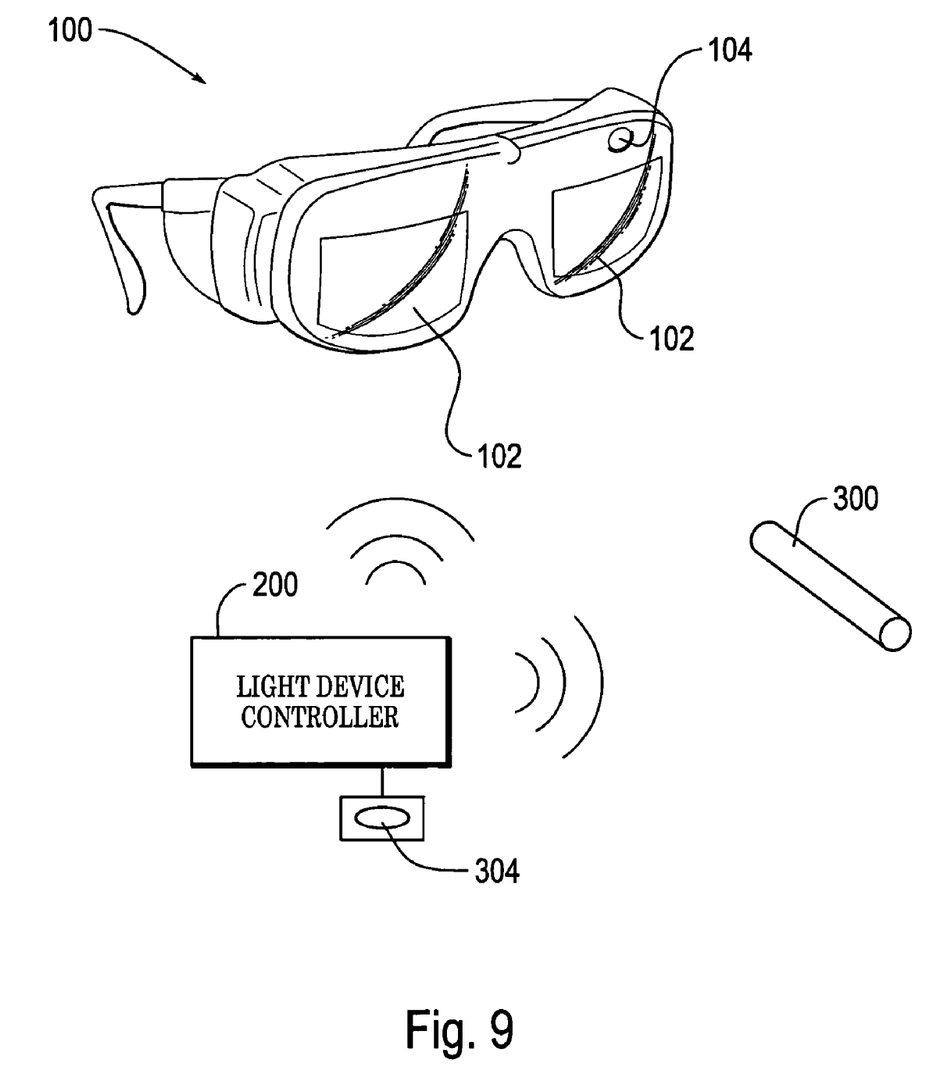
FIG. 9 illustrates a fifth exemplary system according to the invention.

FIG. 9 illustrates a fifth exemplary system according to the invention. Like the system shown in FIG. 8, the system shown in FIG. 9 does not include a separate darken signal transmitter 400. Also, in the system shown in FIG. 9, the light device switch 304 is preferably connected directly to the light device controller 200 and is, for example, a foot-operated switch. When the light device switch 300 is placed in the "ON" state, the light device controller 200 sends wireless signals to each of the eye protection device 100 and the light device 300. A unique signal may be sent to each of the eye protection device 100 and the light device 300, or the same signal may be sent to both. When unique signals are sent, a delay in the signal to the light device 300 may optionally be implemented in hardware and/or software, e.g., in accordance with the principles described above. When the same signal is sent, a delay may optionally be implemented in the light device 300 itself by hardware and/or software, e.g., in accordance with the principles described above.

Although the light device switch 304 is connected directly to the light device controller 200 in FIG. 9, it may alternatively be on the light device 300 as in FIGS. 3, 5, 7 and 8. In this case, the light device 300 would have a transmitter (not shown), and pressing the light device switch 304 would cause a signal to be transmitted to the light device controller 200. The light device controller 200 would, in response to this signal, send out a signal or signals as described above.

Although the light device controller 200 is depicted as being separate from the light device 300 and the eye protection device 100 in FIGS. 8 and 9, it may be instead be included in the light device 300 or the eye protection device 100. Depending on whether it is included in the light device 300 or the eye protection device 100, the light device 300 and the eye protection device 100 are respectively equipped as necessary to enable transmission and/or reception of signals that enable the operation as described above.

While the invention has been described in conjunction with exemplary embodiments, these embodiments should be viewed as illustrative, not limiting. Various modifications, substitutes, or the like are possible within the spirit and scope of the invention.

For example, in the foregoing description, it has been assumed that the see-through state of the selectively darkenable elements 102 is the "default state," i.e., that the selectively darkenable elements 102 are in the see-through state when voltage is not applied, and change to the darkened state when voltage is applied. However, other configurations are also possible, e.g., a configuration in which the darkened state is the default, as described in, for example, U.S. Pat. No. 5,208,688, incorporated herein by reference in its entirety.

It should also be appreciated that, although various embodiments have been depicted each having certain combinations of features, various features of two or more of the depicted embodiments may be combined.

Furthermore, although the specific examples described above are described in the context of non-welding applications, embodiments of the invention are applicable to welding.

What is claimed is:

1. An eye protection apparatus, comprising:
   a selectively darkenable element; and
   a controller that detects a trigger signal that triggers an emission of diffuse light from a diffuse light emission device, and causes transmission of a darken signal that causes the selectively darkenable element to darken in conjunction with the emission of the diffuse light.

2. The eye protection apparatus according to claim 1, wherein the emission of the diffuse light comprises emission of a pulse of the diffuse light.

3. The eye protection apparatus according to claim 1, wherein the darken signal is transmitted prior to the emission of the diffuse light.

4. The eye protection apparatus according to claim 3, wherein the darken signal causes the selectively darkenable element to achieve a darkened state prior to emission of the diffuse light.

5. The eye protection apparatus according to claim 1, wherein a transmission path by which the darken signal is transmitted to the selectively darkenable element comprises a wireless transmission path.

6. The eye protection apparatus according to claim 5, wherein the darken signal comprises an optical signal.

7. The eye protection apparatus according to claim 6, wherein the optical signal comprises a pulse of diffuse light.

8. The eye protection apparatus according to claim 5, wherein the darken signal comprises an acoustic signal.

9. The eye protection apparatus according to claim 5, wherein the darken signal comprises an electromagnetic signal.

10. The eye protection apparatus according to claim 1, further comprising a frame that holds the selectively darkenable element, the frame forming a substantially light-tight seal between a wearer's face and the selectively darkenable element.

11. The eye protection apparatus according to claim 1, wherein the diffuse light is intense diffuse light usable in a medical procedure.

12. The eye protection apparatus according to claim 1, the eye protection apparatus also being capable of protecting the wearer's eyes from at least one pre-selected wavelength of laser light.

13. The eye protection apparatus according to claim 1, wherein:
- the eye protection apparatus is also capable of protecting the wearer's eyes from at least one pre-selected wavelength of laser light;
- the diffuse light is intense diffuse light usable in a medical procedure; and
- the darken signal comprises an acoustic signal.

14. A system, comprising:
- the eye protection apparatus of claim 1;
- the diffuse light emission device, the diffuse light emission device being in communication with the controller by a first path; and
- a switch that transmits the trigger signal when placed in a trigger state; wherein:
- the selectively darkenable element is in communication with the controller by a second path.

15. The system according to claim 14, wherein at least one of the first and second paths is a wireless path.

16. The system according to claim 14, wherein both the first and second paths are wireless paths.

17. The system according to claim 14, wherein both the first and second paths are wired paths.

18. The system according to claim 14, wherein the controller comprises a device that detects a signal passing along the first path.

19. The system according to claim 18, wherein the device is one of a signal splitter and an inductive pick-up device.

20. The system according to claim 14, wherein detection of the trigger signal is implemented using software.

21. The system according to claim 14, wherein the controller, the light emission device and the switch are combined in a single, hand-held unit.

22. The system according to claim 14, wherein:
- the selectively darkenable element and the controller are combined in eyewear; and
- the diffuse light emission device and the switch are in a single, hand-held unit.

23. A method of performing a medical procedure, comprising wearing the eye protection apparatus of claim 1 while performing the medical procedure.

24. An eye protection method, comprising:
- detecting a trigger signal that triggers an emission of diffuse light from a diffuse light emission device; and
- transmitting a darken signal that causes a selectively darkenable element to darken in conjunction with the emission of the diffuse light.

25. The eye protection method according to claim 24, wherein the emission of the diffuse light comprises emission of a pulse of the diffuse light.

26. The eye protection method according to claim 24, wherein the transmission of the darken signal is performed prior to the emission of the diffuse light.

27. The eye protection method according to claim 26, wherein the darken signal causes the selectively darkenable element to achieve a darkened state prior to emission of the diffuse light.

28. The eye protection method according to claim 24, wherein transmitting the darken signal to the darkenable eye protection device comprises transmitting the darken signal via a wireless transmission path.

29. The eye protection method according to claim 28, wherein the darken signal comprises an optical signal.

30. The eye protection apparatus according to claim 29, wherein the optical signal comprises a pulse of diffuse light.

31. The eye protection method according to claim 28, wherein the darken signal comprises an acoustic signal.

32. The eye protection method according to claim 28, wherein the darken signal comprises an electromagnetic signal.

33. An eye protection apparatus, comprising:
- means for detecting a trigger signal that triggers an emission of diffuse light from a diffuse light emission device; and
- means for transmitting a darken signal that causes a selectively darkenable element to darken in conjunction with the emission of the diffuse light.

34. A method of protecting eyes in a medical procedure, comprising:
- wearing a selectively darkenable element that darkens in response to an emission of intense diffuse light from an intense diffuse light emission device and, in a darkened state, protects eyes from the intense diffuse light; and
- performing a medical procedure using the intense diffuse light, causing the selectively darkenable element to be placed in the darkened state.

35. The eye protection method according to claim 34, wherein the intense diffuse light comprises a pulse of diffuse light.

36. The eye protection method according to claim 34, wherein the medical procedure is selected from the group consisting of a hair removal procedure, a tattoo removal procedure, a skin regeneration procedure and a dental procedure.

37. An eye protection apparatus comprising a selectively darkenable element that, in a darkened state, protects a wearer's eyes from intense diffuse light, the eye protection apparatus also being capable of protecting the wearer's eyes from at least one pre-selected wavelength of laser light at a position corresponding to a position of the selectively darkenable element while the selectively darkenable element is in a see-through state.

38. The eye protection apparatus according to claim 37, wherein protection from the at least one pre-selected wavelength of laser light is provided by at least one member selected from the group consisting of a laser protective dye and a laser protective coating.

39. The eye protection apparatus according to claim 37, wherein, when the selectively darkenable element is in a see-through state, the eye protection device has a visible light transmission (VLT) of at least 10% in a viewing direction.

40. The eye protection apparatus according to claim 37, wherein, when the selectively darkenable element is in a see-through state, the eye protection device has a visible light transmission (VLT) of at least 50% in a viewing direction.

41. The eye protection apparatus according to claim 37, wherein, when the selectively darkenable element is in a see-through state, the eye protection device has a visible light transmission (VLT) of at least 80% in a viewing direction.

42. The eye protection apparatus according to claim 37, further comprising a frame that holds the selectively darkenable element, the frame forming a substantially light-tight seal between a wearer's face and the selectively darkenable element.

43. A system, comprising:
the eye protection apparatus of claim 37;
a light emission device that emits diffuse light, the light emission device being in communication with the controller by a first path; and
a switch that transmits the trigger signal when placed in a trigger state; wherein:
the selectively darkenable element is in communication with the controller by a second path.

44. The system according to claim 43, wherein at least one of the first and second paths is a wireless path.

45. The system according to claim 43, wherein both the first and second paths are wireless paths.

46. The system according to claim 43, wherein both the first and second paths are wired paths.

47. The system according to claim 43, wherein the controller comprises a device that detects a signal passing along the first path.

48. The system according to claim 47, wherein the device is one of a signal splitter and an inductive pick-up device.

49. The system according to claim 43, wherein detection of the trigger signal is implemented using software.

50. The system according to claim 43, wherein the controller, the light emission device and the switch are combined in a single, hand-held unit.

51. The system according to claim 43, wherein:
the selectively darkenable element and the controller are combined in eyewear; and
the light emission device and the switch are in a single, hand-held unit.

52. A method of performing a medical procedure, comprising wearing the eye protection apparatus of claim 37 while performing the medical procedure.

53. An eye protection apparatus, comprising:
a selectively darkenable element; and
a controller that causes transmission of a darken signal acoustically or as a flash of low intensity light that causes the selectively darkenable element to darken in conjunction with an emission of intense light by an intense light emission device.

54. The eye protection apparatus according to claim 53, wherein the darken signal is transmitted prior to the emission of the intense light.

55. The eye protection apparatus according to claim 54, wherein the darken signal causes the selectively darkenable element to achieve a darkened state prior to emission of the intense light.

56. The eye protection apparatus according to claim 53, further comprising a frame that holds the selectively darkenable element, the frame forming a substantially light-tight seal between a wearer's face and the selectively darkenable element.

57. The eye protection apparatus according to claim 53, wherein the darken signal is an acoustic signal.

58. The eye protection apparatus according to claim 53, wherein the darken signal is a flash of low intensity light.

59. The eye protection apparatus according to claim 53, wherein the intense light is intense diffuse light.

60. A method of performing a medical procedure, comprising wearing the eye protection apparatus of claim 53 while performing the medical procedure.

* * * * *